United States Patent
McKenna et al.

(10) Patent No.: US 8,880,150 B2
(45) Date of Patent: *Nov. 4, 2014

(54) SYSTEM FOR DETERMINING AN ORIENTATION OF A TRACHEAL TUBE IN A SUBJECT

(71) Applicant: Covidien LP, Mansfield, MA (US)

(72) Inventors: Edward M. McKenna, Boulder, CO (US); Youzhi Li, Longmont, CO (US); Andy Lin, Boulder, CO (US); Sarah Hayman, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,980

(22) Filed: May 16, 2013

(65) Prior Publication Data

US 2013/0253310 A1  Sep. 26, 2013

Related U.S. Application Data

(63) Continuation of application No. 12/420,148, filed on Apr. 8, 2009, now Pat. No. 8,457,715.

(51) Int. Cl.
*A61B 5/00* (2006.01)
*A61M 16/04* (2006.01)
*A61B 5/06* (2006.01)
*A61B 1/267* (2006.01)

(52) U.S. Cl.
CPC .............. *A61M 16/0488* (2013.01); *A61B 5/06* (2013.01); *A61B 1/267* (2013.01); *A61M 16/04* (2013.01); *A61B 5/742* (2013.01); *A61B 5/065* (2013.01); *A61M 16/0434* (2013.01); *A61B 5/0084* (2013.01); *A61M 2205/3306* (2013.01)
USPC .................. 600/424; 128/200.26; 128/207.14

(58) Field of Classification Search
USPC ......................................................... 600/424
See application file for complete search history.

(56) References Cited

U.S. PATENT DOCUMENTS

| 4,344,436 | A | 8/1982 | Kubota |
| 4,416,289 | A | 11/1983 | Bresler |
| 4,431,005 | A | 2/1984 | McCormick |
| 4,445,501 | A | 5/1984 | Bresler |
| 4,567,882 | A | 2/1986 | Heller |

(Continued)

FOREIGN PATENT DOCUMENTS

| WO | 0191843 | 12/2001 |
| WO | 03015610 | 2/2003 |
| WO | 2009099766 | 8/2009 |

OTHER PUBLICATIONS

Roberts, James R. et al., Proper Depth of Placement of Oral Endotracheal Tubes in Adults Prior to Radiographic Confirmation, Academic Emergency Medicine, Jan. 1995, pp. 20-24, vol. 2, No. 1.

(Continued)

*Primary Examiner* — Ruth S Smith
(74) *Attorney, Agent, or Firm* — Fletcher Yoder PC (57) ABSTRACT

According to various embodiments, a tracheal tube may employ optical sensing techniques for determining an orientation of the inserted tube in a subject. The orientation information may provide an indication as to whether or not the tracheal tube is properly placed within the trachea. The optical techniques may include interferometry.

17 Claims, 4 Drawing Sheets

(56) References Cited

U.S. PATENT DOCUMENTS

| | | | |
|---|---|---|---|
| 4,943,770 A | 7/1990 | Ashley-Rollman et al. | |
| 5,099,845 A | 3/1992 | Besz et al. | |
| 5,193,544 A | 3/1993 | Jaffe | |
| 5,400,771 A | 3/1995 | Pirak et al. | |
| 5,425,370 A | 6/1995 | Vilkomerson | |
| 5,425,382 A | 6/1995 | Golden et al. | |
| 5,445,144 A | 8/1995 | Wodicka et al. | |
| 5,560,351 A | 10/1996 | Gravenstein et al. | |
| 5,622,169 A | 4/1997 | Golden et al. | |
| 5,645,065 A | 7/1997 | Shapiro et al. | |
| 5,785,051 A | 7/1998 | Lipscher et al. | |
| 5,879,297 A | 3/1999 | Haynor et al. | |
| 5,902,238 A | 5/1999 | Golden et al. | |
| 6,129,668 A | 10/2000 | Haynor et al. | |
| 6,132,379 A | 10/2000 | Patacsil et al. | |
| 6,161,537 A | 12/2000 | Gravenstein et al. | |
| 6,164,277 A | 12/2000 | Merideth | |
| 6,216,028 B1 | 4/2001 | Haynor et al. | |
| 6,253,770 B1 | 7/2001 | Acker et al. | |
| 6,263,230 B1 | 7/2001 | Haynor et al. | |
| 6,332,089 B1 | 12/2001 | Acker et al. | |
| 6,349,720 B1 | 2/2002 | Clark | |
| 6,453,190 B1 | 9/2002 | Acker et al. | |
| 6,672,308 B1 | 1/2004 | Gaspari | |
| 6,705,319 B1 | 3/2004 | Wodicka et al. | |
| 6,860,264 B2 | 3/2005 | Christopher | |
| 8,244,329 B2* | 8/2012 | Su | 600/424 |
| 8,280,489 B2* | 10/2012 | Li et al. | 600/424 |
| 8,457,715 B2* | 6/2013 | McKenna et al. | 600/424 |
| 8,457,716 B2* | 6/2013 | Li et al. | 600/424 |
| 2002/0074002 A1 | 6/2002 | Tung et al. | |
| 2004/0039252 A1 | 2/2004 | Koch | |
| 2004/0221853 A1 | 11/2004 | Miller | |
| 2005/0177024 A1 | 8/2005 | Mackin | |
| 2006/0036164 A1 | 2/2006 | Wilson et al. | |
| 2006/0081255 A1 | 4/2006 | Miller et al. | |
| 2007/0137652 A1 | 6/2007 | Qureshi et al. | |
| 2008/0039715 A1 | 2/2008 | Wilson et al. | |
| 2008/0273209 A1 | 11/2008 | Delfyett | |

OTHER PUBLICATIONS

Pollard, Richard J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Locker, Gottfried J. MD et al., Assessment of the Proper Depth of Endotracheal Tube Placement with the Trachlight, Journal of Clinical Anesthesia, Aug. 1998, pp. 389-393, vol. 10.

Gaspari, Romolo J. MD et al., Magnetically Guided Orotracheal Intubation, Academic Emergency Medicine, Mar. 2001, pp. 285-287, vol. 8, No. 3.

Salem, M. Ramez MD, Verification of Endotracheal Tube Position, Anesthesiology Clinics of North America, Dec. 2001, pp. 1-18, vol. 19, Issue 4.

Juan, Eduardo J. et al., Miniature Acoustic Guidance System for Endotracheal Tubes, IEEE Transactions on Biomedical Engineering, Jun. 2002, pp. 584-596, vol. 49, No. 6.

Kristensen, Michael S. MD, The Parker Flex-Tip Tube Versus a Standard Tube for Fiberoptic Orotracheal Intubation, Anesthesiology, Feb. 2003, pp. 354-358, vol. 98, No. 2.

Kohase, Hikaru DDS, PhD et al., Endotracheal Intubation Device with a Charge Couple Device Camera, Anesthesiology, Dec. 2003, pp. 432-434, Issue 96.

Makino, Hiroshi MD et al., The Effects of Tracheal Tube Tip Design and Tube Thickness on Laryngeal Pass Ability During Oral Tube Exchanger with an Introducer, Anesthesia and Analgesia, Dec. 2003, pp. 285-288, Issue 97.

Chun, Rosaleen, MDm FRCPC et al., Where's the Tube? Evaluation of Hand-held Ultrasound in Confirming Endotracheal Tube Placement, Prehospital and Disaster Medicine, Nov. 2004, pp. 366-369, vol. 19, No. 4.

Monitoring of Intubation and Ventilation During Resuscitation, http://clinicaltrials.gov/ct2/show/NCT00204217, ClinicalTnals.gov, Aug. 2010, pp. 1-3.

O'Connor, Christopher J. MD et al., Identification of Endotracheal Tube Malpositions Using Computerized Analysis of Breath Sounds via Electronic Stethoscopes, Anesthesia and Analgesia, Dec. 2005, pp. 735-739, Issue 101.

Sehata, H et al., Tracheal Intubation using a new CCD Camera-Equipped Device: A Report of Two Cases with a Difficult Intubation, Acta Anaesthesiologica Scandinavica, Dec. 2005, pp. 1218-1220, Issue 49.

Weaver, Blake et al., Confirmation of Endotracheal Tube Placement after Intubation Using the Ultrasound Sliding Lung Sign, Academic Emergency Medicine, Mar. 2006, pp. 239-244, Issue 13.

Kaplan, M. B. et al., Seeing is Believing: the Importance of Video Laryngoscopy in Teaching and in Managing the Difficult Airway, Surgical Endoscopy and Other Interventional Techniques, Mar. 2006, pp. S479-S483, Issue 20.

Fridman, Ofer, Visual Sensor Provides a Breath of Fresh Air for Medical Ventilation, Medical Design Technology, Jul. 2006, pp. 11-13.

Schwarz, Uwe MD, Validation of Supra-Sternal Tube-Tip Palpatation (SSTTP), http://clinicaltrials.gov/ct2/show/NCT00690508, ClinicalTrials.gov, Aug. 2010, pp. 1-4.

Karsli, Cengiz, Head Movement Effect on Different Tracheal Tubes, http://clinicaltrials.gov/ct2/show/NCT00687583, ClinicalTrials.gov, Aug. 2010, pp. 1-3.

Wichakook, Warit et al., Magnetic Endotracheal Tube Imaging Device, 30th Annual International IEEE EMBS Conference, Vancouver, Canada, Aug. 20-24, 2008, pp. 985-988.

* cited by examiner

SYSTEM FOR DETERMINING AN ORIENTATION OF A TRACHEAL TUBE IN A SUBJECT

CROSS REFERENCE TO RELATED APPLICATION

This application is a continuation of U.S. Pat. No. 8,457,715, filed Apr. 8, 2009, entitled "Medical Device and Technique for Using the Same," in the name of Edward McKenna et al., which is incorporated by reference herein in its entirety.

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated when an endotracheal tube is inserted through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube's position within the trachea that may occur when a patient coughs, which may dislodge a tube from its desired location, or when a patient is jostled or moved within a care setting, which may change the position or angle of the tube within the trachea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient's trachea at a location substantially between the patient's vocal cords and carina. If the tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Provided herein are tracheal tubes and systems for facilitating proper placement of the tracheal tube relative to certain anatomical structures in and around the patient's airway and trachea. Such tracheal tubes may include assemblies for shining coherent light into the trachea and detecting the returned light. The light is returned after being reflected/scattered by internal tissues of the patient (such as the tissues in the vicinity of the carina). Accordingly, information related to the detected light, for example its phase relative to a reference, may be used to determine a distance from the tube to the anatomical structure in question. In embodiments, a distance from the distal end of the tracheal tube to the carina (or other internal anatomical structure or tissue) may be determined. A healthcare provider may then use the information about the location of the tracheal tube relative to the anatomical structures (e.g., the carina) to determine whether the tube is properly placed or whether the position of the tube should be adjusted.

In embodiments, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
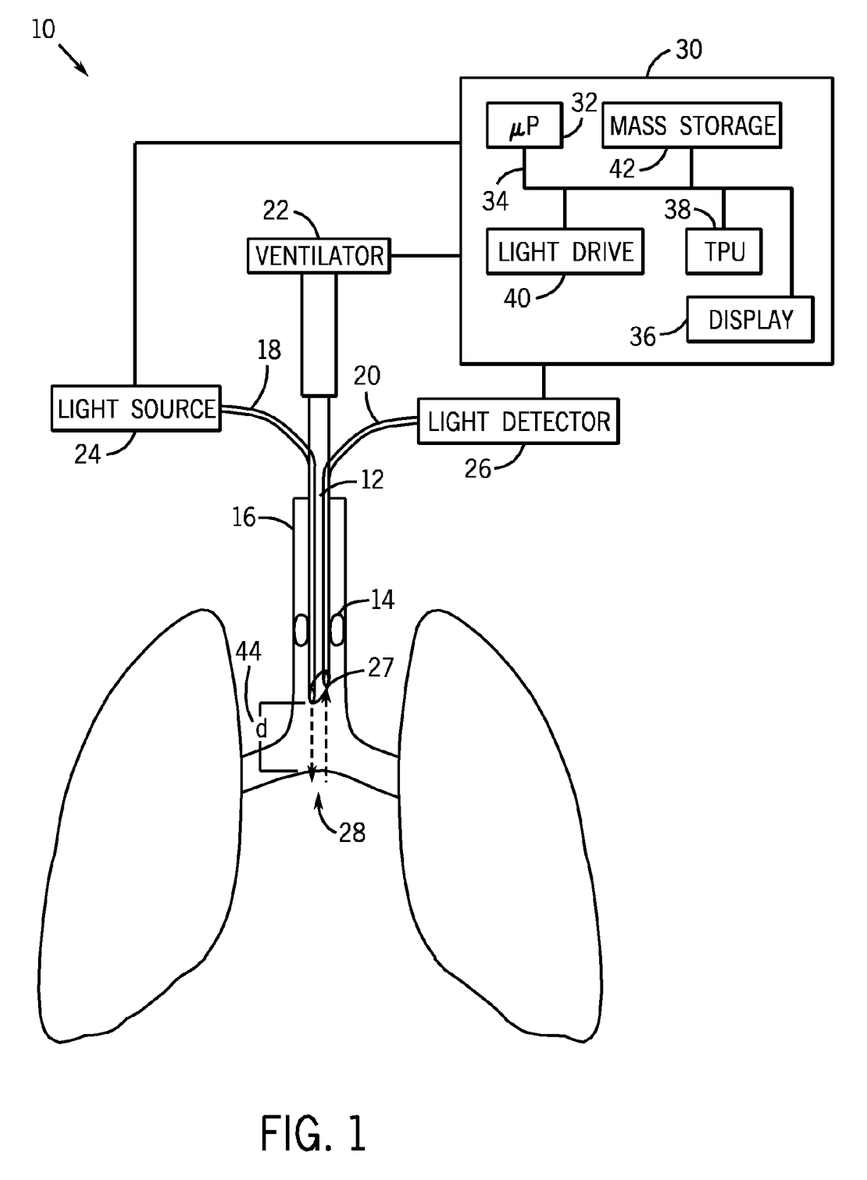
FIG. 1 illustrates an exemplary system including an endotracheal tube with a coherent light source and detector according to embodiments.

FIG. 1 shows an exemplary tracheal tube system 10 that has been inserted into a patient's trachea. The system 10 includes a tracheal tube 12, shown here as endotracheal tube, with an inflatable balloon cuff 14 that may be inflated to form a seal against tracheal walls 16. The tracheal tube 12 may also include one or more optical conductors, e.g., optical source fibers 18 and optical detection fibers 20 that are associated with the tube 12. When ventilation is provided via the tube system, a ventilator 22 is typically provided, as discussed below. The optical source fiber 18 may be configured to pass light from a source 24 through a distal end 27 of the endotracheal tube and into a patient's trachea such that a portion of the emitted light may interact with a carina 28. The emitted light may be transferred back through the optical detection fiber 20, which may be coupled to a light detector 26.

When the system 10 includes devices that facilitate positive pressure ventilation of a patient, such as ventilator 22, any ventilator may be used, such as those available from Nellcor Puritan Bennett LLC. The system may also include a monitor 30 that may be configured to implement embodiments of the present disclosure. The monitor 30 may be a stand-alone device or may be coupled to another patient monitor or to the ventilator 22. The monitor 30 may include a microprocessor 32 coupled to an internal bus 34 and a display 36. Regardless of where it is placed, the microprocessor, or any other suitable processing circuitry, aids in computing the distance of the distal end 27 of the tube from reference structures within the patient, such as the carina 28.

The monitor 30 may include certain elements for controlling the light source 24 and the light detector 26. The monitor 30 may drive light from source 24, which in turn may be carried by optical source fiber 18. The light may pass into the tissue, where it may be variously scattered, absorbed, and/or reflected and then detected by detector 26. A time processing unit (TPU) 38 may provide timing control signals to light drive circuitry 40, which controls when the light source 24 is activated, and if multiple light sources 24 are used, the multiplexed timing for the different light sources. TPU 38 may also control the gating-in of signals from detector 26.

The monitor 30 may be configured to receive signals from the detector 26 and store the signals in a mass storage device 42, such as a RAM, ROM, optical storage device, flash memory device, hardware storage device, a magnetic storage device, or any other suitable device permitting memory storage. The signals may be accessed and operated according to instructions (which may also be stored in the memory circuitry) executed by the microprocessor 32. In certain embodiments, the signals may be related to a placement of the tracheal tube 12 within the patient's trachea and may be processed by the monitor 30 to indicate whether the tracheal tube 12 is properly placed. The monitor 30 may be configured to provide an indication about the placement of the tracheal tube 12 within the patient's trachea, such as an audio alarm, visual alarm or a display message if the tracheal tube 12 is too far or too close to certain anatomical structures, such as the carina 28, or outside of a predetermined placement range. In an embodiment, based at least in part upon the received signals corresponding to the light received through optical detection fiber 20, microprocessor 32 may calculate a placement parameter of the endotracheal tube 12 using various algorithms. The placement parameter may relate to, measure, or provide an indication of a distance 44 between the distal end 27 of the tube 12 and the carina 28 or other anatomical structure.

Figure 2:
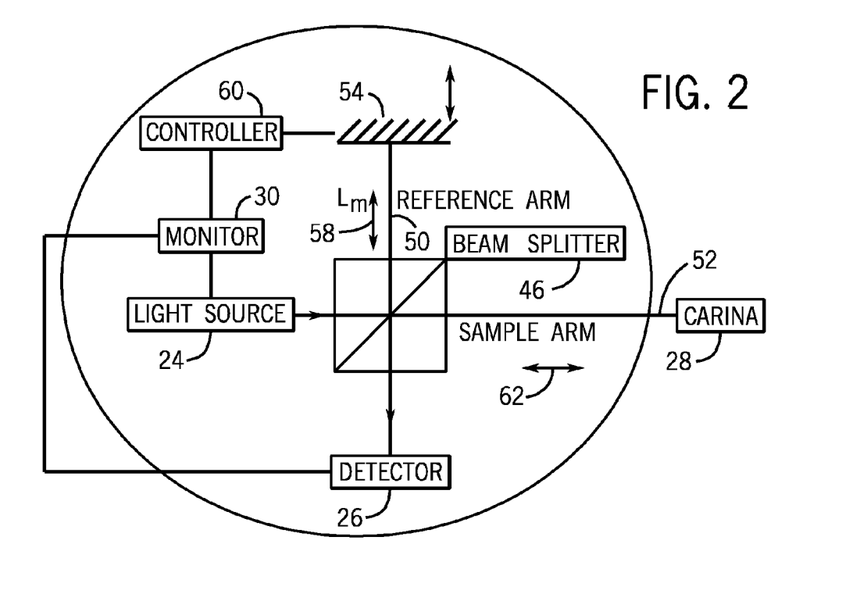
FIG. 2 is a schematic diagram of an interferometer that may be coupled to a tracheal tube according to embodiments.

FIG. 2 is a schematic representation of an exemplary interferometry arrangement that may be incorporated into system 10 for analyzing placement of a tracheal tube 12 within a patient's trachea. In general, a reference beam may be combined with a sample beam to generate interference peaks, corresponding to the measured distance. In the depicted arrangement, a beam splitter 46 divides light from light source 24 between a reference beam 50 and the sample beam 52. The reference beam is configured to impinge a reflective surface 54 (e.g., a mirror), which is a distance Lm from the detector 26. In one embodiment, the beam splitter 46 may be configured to emit the reference beam 50 towards the reflective surface 54, for example along an axis 58 in a direction substantially orthogonal to the sample beam 52. In such an embodiment, the placement of the reflective surface 54 may also be generally orthogonal to the axis 62 of the sample beam 52. The distance Lm may change as the reflective surface 54 is moved toward or away from the detector 26. The reflective surface 54 may be under the control of a reference beam controller 60 that may control the movement of reflective surface 54 and may be in communication with monitor 30, which includes light drive circuitry 32 for driving light source 24. The reference beam controller 60 may provide information to the monitor 30 about changes in the distance Lm. It should be understood that the depicted arrangement is merely an example of a particular low-coherence interferometry arrangement and other suitable arrangements may be employed. For example, in certain embodiments, a 2×2 fiber coupler may be used in place of a beam splitter 46. For the fiber coupler case, the beams may run along any axis since fibers may be flexible. Accordingly, orthogonal relationships between reference and sample arms may not hold. However, light emitted from a fiber may be normal to the reflective surface 54 in order to have the reflected light coupled back into the fiber.

The light that is reflected from the mirror 54 may impinge a detector 26 to generate the reference signal, while the light that is returned through optical detection fiber 20 may impinge a detector 26 to generate the sample signal. In one embodiment, the sample signal and the reference beam signal are both generated at a single detector 26. In one embodiment, TPU 38 may control gating-in of the reference beam signal and the sample signal. Both signals are combined and directed to the detector 26, which will typically include one or more photodetectors (e.g., photodiodes) that generate measurement signals based upon the received radiation. The reference signal and sample signal may be analyzed by the microprocessor 32 (e.g, via the measurement signal from the detector). In one embodiment, the signals may be combined to form an interferogram. At the point of maximum interference between the reference signal and the sample signal, it may be determined that the distance Lm is substantially equal to a distance Lc, which may be defined as a distance between an end of the tube and the carina 28. Because Lm is known, Lc may be determined, as discussed in more detail below.

The light source 24 and a detector 26 may be of any suitable type. For example, the light source 24 may be one or more light emitting diodes adapted to transmit one or more wavelengths of light, for example in the red to infrared range, and the detector 26 may be one or more photodetectors selected to receive light in the range or ranges emitted from the light source 24. A light source 24 may be a coherent light source, such as a laser diode or a vertical cavity surface emitting laser (VCSEL). The light source 24 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra. In one example of a low-coherence interferometry arrangement, the light source 24 may include a low-coherence laser source such as a Nd:YVO$_4$ pumped titanium: sapphire laser that yields radiation having a wavelength range from approximately 650 nm to approximately 900 nm after passing through a fiber.

Figure 3:
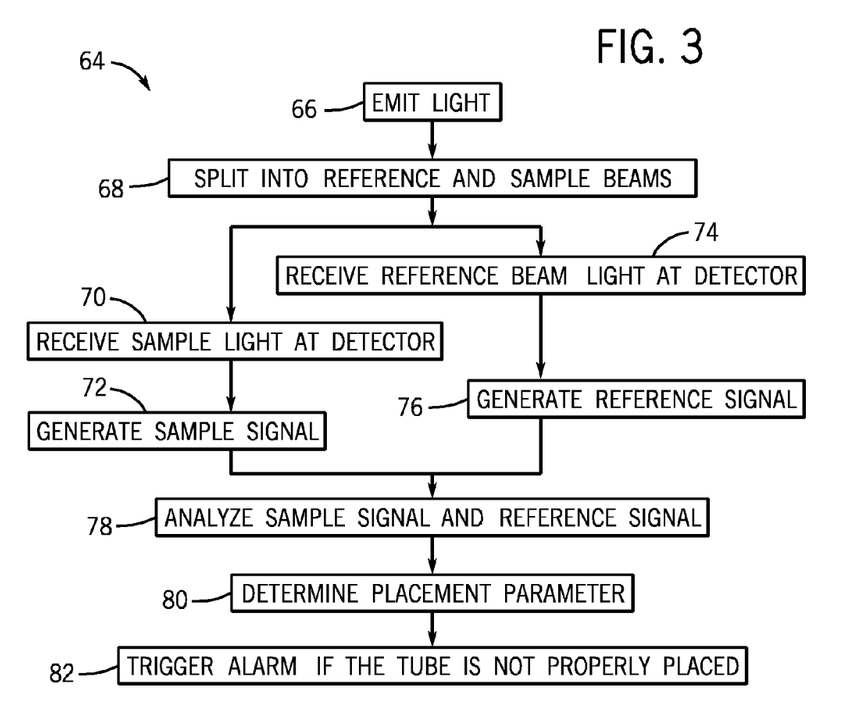
FIG. 3 is a flow diagram of a method of operating a tracheal tube according to embodiments.

FIG. 3 is a process flow diagram illustrating a method in accordance with some embodiments. The method is generally indicated by reference number 64 and includes various steps or actions represented by blocks. It should be noted that the method 64 may be performed as an automated procedure by a system, such as system 10. Further, certain steps or portions of the method may be performed by separate devices. For example, a first portion of the method 64 may be performed by a light source 24 and light detector 26, while a second portion of the method 64 may be performed by a monitor 30. In embodiments, the method 64 may be performed continuously or intermittently for long-term patient monitoring or at any appropriate interval depending on the particular situation of the intubated patient. Further, the steps of method 64 may be performed during insertion of the tracheal tube 12 into the patient.

According to an embodiment, the method 64 begins with emitting light, such as coherent light, at step 66 from a light source 24 coupled to one or more optical fibers 18. The emitted light is split at step 68 into a reference light beam 50 and a sample beam 52. The sample beam is transmitted through fiber 18, which is associated with tube 12 that is inserted into a patient's airway. The sample beam 52 may exit the distal end 27 of the tube 12 before interacting with anatomical structures in the patient. Any light that is returned through detection fiber 20 and received by the detector 26 at step 70 may carry information about the relative position of the tube 12 and the anatomical structure that is carried in the sample signal, generated at step 72. At step 74, the reference beam 50 is detected by the detector 26 to generate the reference signal at step 76. In an alternative arrangement, reference light beam 50 and the sample beam 52 may be combined at the detector 26 to yield interference peaks (e.g., an interferogram). Accordingly, in certain arrangements, steps 72 and 76 may be at least partially combined.

A monitor 30 may perform analysis of the sample signal and the reference signal at step 78. In embodiments, the monitor may amplify and/or filter one or both of the sample signal and the reference signal prior to the analysis, as well as the measurement signal generated by combining the two. In one embodiment, an interferogram may be generated by the monitor 30. The interferogram may be used to determine the point of maximum interference between the sample signal and the reference signal. Generally, this point may correspond to a point where a distance between an emitter 24 and the carina 28, Lc, is substantially equal to a distance between a reflective surface 54 and a detector 26, Lm. However, certain arrangements using beamsplitters, fiber couplers, or optical fibers may influence the determinations of Lm or Lc. In certain implementations, once the light is split by the beam splitter 46 or a fiber coupler, Lm is the distance between the beam splitting point and the reflective surface 54, while Lc is the distance from the carina 28 to the same beam splitting point. It should also be understood that, because the emitter 24 and detector 26 may be coupled to optical fibers that may not substantially alter the intensity of light as a function of their length, in embodiments, determining the distance 44 from Lc may involve subtracting a length of the optical fiber. That is, the measured length or distance can be easily converted to a distance 44 between the end of the tube and the anatomical structure of interest by subtracting the light transmission length represented by the optical fibers, any connectors, and so forth.

A monitor 30 may use the distance Lc as a placement parameter at step 80 to determine whether this distance is acceptable by reference to a desirable placement of the tracheal tube 12. Example of placement parameters may include a calculated distance between a tube 12 and an anatomical structure. In one embodiment, a placement parameter may be a ratio of a calculated distance 44 determined from Lc and an empirically derived or clinically measured distance associated with proper tube placement. For example, proper tube placement may involve a measured distance 44 of 1-5 cm. It should be appreciated that there may be several empirically derived target distances, depending on the size, age, or sex of the patient. A target distance to which the measured distance 44 may be compared may differ for adult men, who may have, in an embodiment, a predetermined target of 3-4 cm, and adult women, for whom the predetermined target may be 2-3 cm. In other embodiments, the alarm may be triggered if the measured distance 44 is less than 3 cm, less than 2 cm, or less than 1 cm.

A placement parameter may also be an average or mean of multiple data points or measurements. A placement parameter may also include a graphical, visual, or audio representation of the tube/anatomical structure distance. For example, a placement parameter associated with proper placement may include green light indicated on a display or a short tone generated by a speaker associated with monitor 30. Similarly, a placement parameter associated with improper placement of the tube 12 may trigger an alarm at step 82, which may include one or more of an audio or visual alarm indication. In one embodiment, the alarm may be triggered if the placement parameter is, substantially less than or substantially greater than a predetermined value, or outside of a predetermined range.

In one embodiment, the controller 60 may collect interferometry data at multiple reference mirror 54 positions and the data may form multiple reference signals. That is, the distance Lm traveled by the reference beam may be varied and matched to the distance Lc to the anatomical feature such that the two remain matched during intubation, providing a substantially continuous measurement of the distance of interest. Such measurements may include closed-loop control of the length of the reference length Lm by appropriate control of the mirror. For example, such an embodiment may be employed for determining a placement parameter during intubation. As the tube 12 is inserted into the patient, the mirror 54 may be moved until the distance Lc is equal to the distance Lm. For low coherence interferometric measurement, the reflective surface 54 may be continuously scanned back and forth. The interference peaks will move, corresponding to the distance Lc changes. For applications involving real time analysis during intubation, spectral detection with a CCD detector array or accelerated digitization and processing using a field-programmable gate array (FPGA) may be used.

Figure 4:
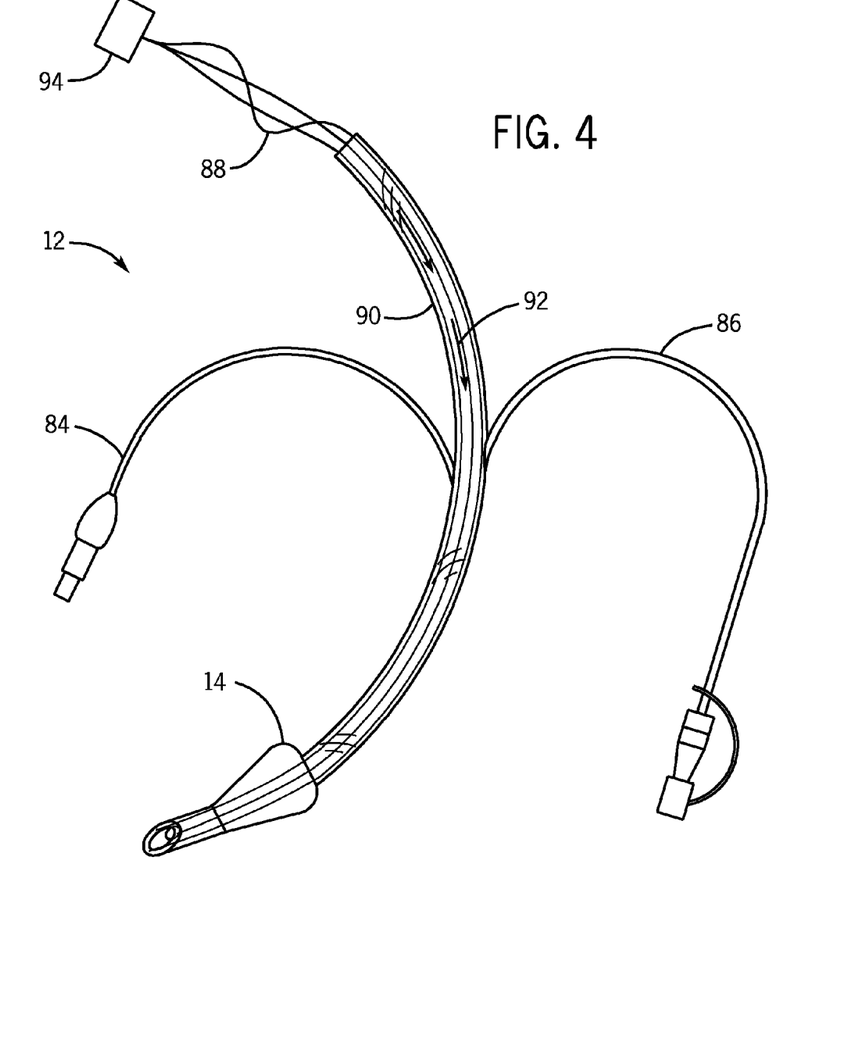
FIG. 4 is a perspective view of an exemplary endotracheal tube of FIG. 3.

FIG. 4 is a perspective view of an exemplary tracheal tube 12 according to certain embodiments. As shown, the tube 12 may include a cuff 14 that may be inflated via inflation lumen 84. The tracheal tube 12 may also include a suction lumen 86 for aspirating secretions that may form above the cuff 14. The tracheal tube 12 may also include a plurality of fiber bundles 88. In certain embodiments, individual fibers rather than fiber bundles 88 may be used. Each fiber bundle may include one or more optical source fibers 18 and optical detection fibers 20. In certain embodiments, the transmitting and detecting may also take place within a single fiber. As shown, the fiber bundles 88 may extend through the walls 90 of the tracheal tube 12 such that they are substantially in line with a flow path 92 of the tracheal tube 12. The fiber bundles 88 may include any appropriate optical connector 94 for connecting the fiber bundles 88 to components of the system 10, such as the beam splitter 46 or the light source 24 or light detector 26.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In one embodiment, the cuff 14 may be generally sized and shaped as a high volume, low pressure cuff that may be designed to be inflated to pressures between about 15 cm $H_2O$ and 30 cm $H_2O$. The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 5:
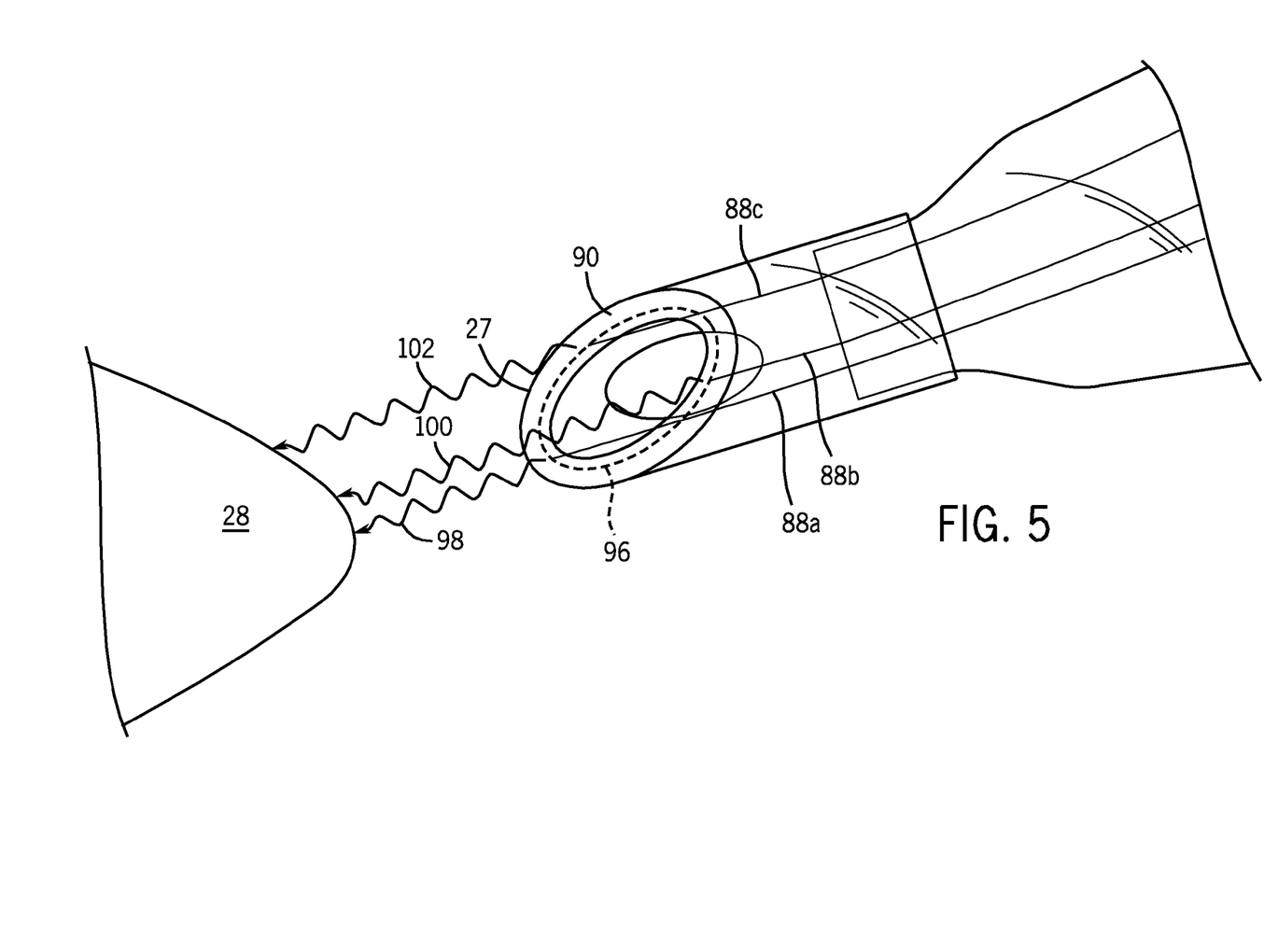
FIG. 5 is a perspective view of an exemplary distal tip of a tracheal tube with embedded optical fibers that may be coupled to a coherent light source and photodetector.

FIG. 5 is a side view of the distal end 27 of the tracheal tube 12. As shown, the fiber bundles 88 may extend through the walls 90 of the tracheal tube. In certain embodiments, the fiber bundles 88 may be embedded or coextruded within an extruded tube tracheal tube 12. When the tube 12 is manufactured, the distal end 27 may be cut on a slant to facilitate insertion of the tube 12 in the trachea. After the tube is cut, the fiber bundles 88 may be terminated by any suitable technique.

The fiber bundles 88, or in certain embodiments, individual fibers rather than fiber bundles 88, may be distributed around the circumference 96 of the tube wall 90. In an embodiment, three optical bundles may be substantially evenly spaced about the circumference 96. As shown, the positioning of the fiber bundles 88 or single fibers may influence the path of the light from the distal end 27 of the tube 12 to the anatomical structure. Arrows 98, 100, and 102 illustrate three different light paths from bundles 88a, 88b, and 88c, respectively, to anatomical structures at or proximate to the carina 28. Arrow 98 has a somewhat shorter path than arrow 100, which is related to its position around the circumference 96 relative to the carina 28, as well as differences in the topography of the carina 28. In addition, slight changes in the angle within the trachea of the distal end 27 of the tube 12 may influence the path of light to and from the fiber bundles 88. In certain embodiments, light detected from all three fiber bundles 88 may be combined or averaged to generate the data used to determine a placement parameter. In addition, the differences in path length between multiple bundles may be used to determine a placement parameter that is indicative of the orientation of the distal end 27 within the trachea. Changes in this orientation (e.g., angular displacement) may indicate a shift in tube placement that may influence cuff pressure and sealing.

In certain embodiments, the fibers or fiber bundles 88 may be formed from materials such as quartz, glass, or a transparent plastic, such as poly(methyl methacrylate) or polystyrene with a fluoropolymer cladding. Examples of optical fibers include single-mode fibers, multi-mode fibers, photonic-crystal fibers, hollow-core fibers, polarization-maintaining fibers and dual-clad fibers. Typical diameters for optical fibers are from 5 to 1,000 micrometers. The optical fiber may be a single-mode fiber or a multi-mode fiber.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube placement relative to anatomical structures in the trachea, but these techniques may also be utilized for the measurement and/or analysis of the placement of other suitable medical devices relative to other anatomical structures. For example, the present techniques may be utilized for the measurement and/or analysis of tracheal tubes relative to tracheal walls or the vocal cords. In addition, the present techniques may be employed in determining appropriate placement of any medical device, such as a stent, catheter, implant, feeding tube, cardiac device, drug delivery device, or pump. Rather, the various embodiments may cover all modifications, equivalents, and alternatives falling within the spirit and scope of the disclosure as defined by the following appended claims.

What is claimed is:

1. A medical device for determining an orientation of a tracheal tube in a subject comprising:
    a processor configured to execute instructions for:
        driving a light source to emit light through a plurality of optical conductors circumferentially spaced apart on a beveled distal end of the tracheal tube, wherein the beveled distal end is slanted relative to a wall of the tracheal tube;
        receiving information related to received light at a detector for each of the plurality of optical conductors;
        receiving information related to an interference between the received light and a reference beam; and
        determining an orientation of the tracheal tube based upon the interference between the received light and the reference beam for each of the plurality of optical conductors and a difference in path length between the plurality of optical conductors, wherein the difference in path length is representative of a position of each respective optical conductor about the beveled distal end; and
    a memory storing the instructions, wherein the memory is coupled to the processor;
    wherein the processor is configured to access the memory to read the instructions.

2. The medical device of claim 1, comprising a moving reflective surface, and wherein the processor is configured to execute instructions for determining a distance between a distal end of each of the plurality of optical conductors and an anatomical structure of the subject by altering a distance traveled by the reference beam between the moving reflective surface and the detector, and determining a point of maximum interference between the received light for each of the plurality of optical conductors and the reference beam.

3. The medical device of claim 1, wherein the processor is configured to execute instructions for determining a distance between the tracheal tube and a carina of the subject.

4. The medical device of claim 3, wherein the processor is configured to execute instructions for triggering an alarm when the distance between the tracheal tube and the carina is less than a first predetermined distance or greater than a second predetermined distance.

5. The medical device of claim 1, comprising a display configured to display an indication of the orientation.

6. The medical device of claim 1, comprising the plurality of optical conductors, a light source coupled to the plurality of optical conductors, and light drive circuitry configured to drive the light source.

7. The medical device of claim 6, comprising a beam splitter configured to divide light from the light source into a sample beam and the reference beam.

8. The medical device of claim 1, comprising the plurality of optical conductors, wherein each of the plurality of optical conductors comprises an optical fiber bundle comprising at least one emitting fiber and at least one return fiber.

9. The medical device of claim 1, wherein the processor is configured to execute the instructions during intubation of the subject.

10. The medical device of claim 1, wherein the processor is configured to execute the instructions after intubation of the subject.

11. A system for determining an orientation of a tracheal tube in a subject comprising:
a tracheal tube comprising a plurality of optical conductors circumferentially spaced apart on a beveled distal end of the tracheal tube, wherein the beveled distal end is slanted relative to a gas flow pathway of the tracheal tube;
a light source configured to emit coherent light through each of the respective plurality of optical conductors when the tracheal tube is disposed in the subject;
a photodetector configured to receive returned coherent light emitted from each of the respective plurality of optical conductors and returned light from a reference beam for each of the plurality of optical conductors; and
a processor configured to determine an orientation of the tracheal tube based upon an interference between the returned coherent light and the reference beam for each of the plurality of optical conductors and a difference in path length between the plurality of optical conductors, wherein the difference in path length is representative of a position of each respective optical conductor about the beveled distal end of the tracheal tube.

12. The system of claim 11, wherein the processor is configured to determine distances between a plurality of points on the beveled distal end of the tracheal tube and one or more anatomical structures within the subject based upon the interference between the returned coherent light emitted from the respective plurality of optical conductors and the reference beam.

13. The system of claim 11, comprising a beam splitter configured to split a portion of the emitted coherent light into the reference beam.

14. The system of claim 11, comprising a moving reflective surface, wherein the processor is configured to determine a distance between the tracheal tube and an anatomical structure within the subject by altering a distance traveled by the reference beam between the moving reflective surface and the photodetector, and determining a point of maximum interference between the returned coherent light emitted from the respective plurality of optical conductors and the reference beam.

15. A system comprising:
a tracheal tube;
a plurality of optical conductors circumferentially spaced apart on a beveled distal end of the tracheal tube, wherein the beveled distal end is slanted relative to a gas flow pathway of the tracheal tube;
a light source configured to emit light through the plurality of optical conductors;
a beam splitter configured to split a portion of the emitted light into a reference beam;
a light detector configured to receive light emitted from each of the plurality of optical conductors that has interacted with an anatomical structure of the subject, to generate a sample signal for each respective optical conductor based on the received light, to receive light from the reference beam, and to generate a reference signal based on the received light from the reference beam;
a monitor coupled to the light source and the light detector, wherein the monitor comprises:
drive circuitry for driving the light source; and
a processor configured to receive signals from the light detector and determine an orientation of the tracheal tube based at least in part on an interference between the sample signal from each respective optical conductor and the reference signal and a difference in path length between the plurality of optical conductors, wherein the difference in path length is representative of a position of each respective optical conductor about the beveled distal end of the tracheal tube.

16. The system of claim 15, wherein one or more of the plurality of optical conductors are disposed within a wall of the tracheal tube.

17. The system of claim 15, wherein the plurality of optical conductors are evenly spaced about a circumference of a wall of the tracheal tube.

* * * * *